US012282591B2

(12) United States Patent
Durfee (10) Patent No.: US 12,282,591 B2
(45) Date of Patent: Apr. 22, 2025

(54) ALTERNATIVE-REALITY DEVICES AND METHODS FOR ESTABLISHING AND VISUALIZING HISTORICAL SITES OF VASCULAR ACCESS (71) Applicant: Bard Access Systems, Inc., Salt Lake City, UT (US)

(72) Inventor: Tyler L. Durfee, Stansbury, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 845 days.

(21) Appl. No.: 17/391,945

(22) Filed: Aug. 2, 2021

(65) Prior Publication Data
US 2022/0031965 A1 Feb. 3, 2022

Related U.S. Application Data (60) Provisional application No. 63/060,631, filed on Aug. 3, 2020.

(51) Int. Cl.
*G06F 3/01* (2006.01)
*A61B 5/00* (2006.01)
(Continued)

(52) U.S. Cl.
CPC .............. *G06F 3/011* (2013.01); *A61B 5/743* (2013.01); *A61M 5/427* (2013.01); *G06T 7/73* (2017.01);
(Continued)

(58) Field of Classification Search
None
See application file for complete search history.

(56) References Cited

U.S. PATENT DOCUMENTS

2009/0138282 A1 5/2009 Lee
2015/0209113 A1 7/2015 Burkholz et al.
(Continued)

FOREIGN PATENT DOCUMENTS

WO 2017/151963 A1 9/2017

OTHER PUBLICATIONS

PCT/US2021/044201 filed Aug. 2, 2021 International Search Report and Written Opinion dated Nov. 19, 2021.

*Primary Examiner* — Jwalant Amin
(74) *Attorney, Agent, or Firm* — Rutan & Tucker LLP (57) ABSTRACT

Alternative-reality devices and methods are disclosed for establishing and visualizing historical sites of vascular access, which are useful for evaluating potential sites of vascular access and improving the successes of obtaining vascular access. For example, an alternative-reality device includes anatomical target-defining instructions and vascular access site-tracking instructions in memory of the alternative-reality device for execution by one-or-more processors thereof. The alternative-reality device also includes a patient-facing camera configured to capture images or video frames for generating an anatomical target in the memory per the anatomical target-defining instructions and tracking the historical sites of vascular access in relation thereto with the vascular access site-tracking instructions. With a display screen of the alternative-reality device, a user can instantly see an environment including an anatomical portion of a patient to which the anatomical target corresponds, as well as graphical elements anchored to the anatomical portion indicating the historical sites of vascular access.

21 Claims, 4 Drawing Sheets (51) Int. Cl.
*A61M 5/42* (2006.01)
*G06T 7/73* (2017.01)
*G06T 19/00* (2011.01)
*G06T 19/20* (2011.01)
*G06V 20/20* (2022.01)

(52) U.S. Cl.
CPC ............ *G06T 19/006* (2013.01); *G06T 19/20* (2013.01); *G06V 20/20* (2022.01); *A61M 2205/507* (2013.01); *G06T 2200/24* (2013.01); *G06T 2207/30101* (2013.01); *G06T 2210/41* (2013.01); *G06T 2219/2012* (2013.01)

(56) References Cited

U.S. PATENT DOCUMENTS

| | | |
|---|---|---|
| 2017/0028141 A1* | 2/2017 | Fiedler ................. A61M 5/003 |
| 2017/0259013 A1* | 9/2017 | Boyden ................. G16H 30/40 |
| 2019/0143052 A1 | 5/2019 | McClellan |
| 2019/0282324 A1 | 9/2019 | Freeman et al. |
| 2019/0307419 A1 | 10/2019 | Durfee |
| 2020/0316316 A1* | 10/2020 | Haverman ........... G06V 10/143 |

* cited by examiner

ALTERNATIVE-REALITY DEVICES AND METHODS FOR ESTABLISHING AND VISUALIZING HISTORICAL SITES OF VASCULAR ACCESS

PRIORITY

This application claims the benefit of priority to U.S. Provisional Patent Application No. 63/060,631, filed Aug. 3, 2020, which is incorporated by reference in its entirety into this application.

BACKGROUND

Vascular access by way of, for example, insertion of a catheter into a peripheral blood vessel provides an effective means for withdrawing blood, transfusing blood, delivering medications, or providing nutrition to a patient over a period of days, weeks, or even months. However, vascular access is not always so easily obtained. For example, vascular access can be particularly difficult to obtain if the patient is older, obese, or hypotensive. It can also be particularly difficult to obtain vascular access if the patient is an intravenous drug abuser or has one or more injuries limiting potential sites for vascular access. It would be helpful to be able instantly visualize historical sites of vascular access and the successes and failures thereof in obtaining vascular access.

Disclosed herein are alternative-reality devices and methods for establishing and visualizing historical sites of vascular access, which are useful for evaluating potential sites for vascular access and improving the successes of obtaining vascular access.

SUMMARY

Disclosed herein is an alternative-reality device for establishing and visualizing historical sites of vascular access. The alternative-reality device includes a mechanical support, a patient-facing camera operably coupled to the mechanical support, and a display screen operably coupled to the mechanical support. The mechanical support supports electronic components including memory and one or more processors communicatively coupled by electronic circuitry of the alternative-reality device. The memory includes anatomical target-defining instructions and vascular access site-tracking instructions for execution by the one-or-more processors. The patient-facing camera is configured to capture one or more images, video frames, or a combination thereof. The one-or-more images, video frames, or the combination thereof are for generating an anatomical target in a corresponding target data file in the memory in accordance with the anatomical target-defining instructions. The one-or-more images, video frames, or the combination thereof are also for tracking the historical sites of vascular access in relation to the anatomical target in accordance with the vascular access site-tracking instructions. With the display screen, a user of the alternative-reality device can instantly see an environment including an anatomical portion of a patient to which the anatomical target corresponds. The display screen is configured to display one or more graphical elements anchored to the anatomical portion of the patient to indicate at least the historical sites of vascular access.

In some embodiments, the anatomical target is defined in the target data file by a number of feature points corresponding to anatomical features identified in the one-or-more images, video frames, or the combination thereof for the anatomical portion of the patient.

In some embodiments, the anatomical features include topographical features selected from veins, moles, scars, and skinfolds, skin-contrasting features selected from veins, moles, scars, and skinfolds, or a combination thereof.

In some embodiments, the historical sites of vascular access are defined in the target data file by a number of needle-stick points in relation to the feature points. The needle-stick points correspond to needle-stick locations identified in the one-or-more images, video frames, or the combination thereof during a vascular-access procedure or manually entered into the alternative-reality device by the user after the vascular-access procedure.

In some embodiments, the one-or-more graphical elements are visually differentiated among at least graphical elements for successful sites of vascular access and unsuccessful sites of vascular access among the historical sites of vascular access.

In some embodiments, the successful sites of vascular access are represented on the display screen by green dots anchored to the anatomical portion of the patient and the unsuccessful sites of vascular access are represented on the display screen by red dots anchored to the anatomical portion of the patient.

In some embodiments, the memory further includes vascular access site-suggesting logic for execution by the one-or-more processors. The vascular access site-suggesting logic is configured to suggest to the user a number of potential sites for vascular access on the display screen with the one-or-more graphical elements in view of the historical sites of vascular access.

In some embodiments, the alterative-reality device is a headset, the mechanical support is a printed circuit board disposed in a frame of the headset, and the display screen is a see-through display screen coupled to the frame through which the user can see the environment including the patient.

In some embodiments, the alternative-reality device is a smartphone, the mechanical support is a printed circuit board disposed in a housing of the smartphone, and the display screen is a built-in display screen coupled to the housing upon which the user can see the environment including the patient.

In some embodiments, the alternative-reality device includes a wireless communication module for wirelessly transferring the target data file to a network-connected computer system and updating an electronic medical record.

Also disclosed herein is a method of an alternative-reality device. The method includes an anatomical target-generating step, an anatomical target-storing step, a vascular access site-tracking step, and a displaying step. The anatomical target-generating step includes generating an anatomical target from an anatomical portion of a patient in one or more images, video frames, or a combination thereof obtained from a patient-facing camera of the alternative-reality device. The anatomical target-generating step is performed upon executing anatomical target-defining instructions stored in memory of the alternative-reality device by one or more processors thereof. The anatomical target-storing step includes storing the anatomical target in a corresponding target data file in the memory. The vascular access site-tracking step includes tracking sites of vascular access from the one-or-more images, video frames, or the combination thereof in relation to the anatomical target in the target data file. The vascular access site-tracking step is performed upon executing vascular access site-tracking instructions stored in the memory by the one-or-more processors. The graphical element-displaying step includes displaying on a display screen of the alternative-reality device one or more graphical elements anchored to the anatomical portion of the patient in an environment thereof to indicate to a user of the alternative-reality device at least historical sites of vascular access.

In some embodiments, the anatomical target-generating step includes defining the anatomical target in the target data file by a number of feature points corresponding to anatomical features of the anatomical portion of the patient identified in the one-or-more images, video frames, or the combination thereof.

In some embodiments, the anatomical features include topographical features selected from veins, moles, scars, and skinfolds, skin-contrasting features selected from veins, moles, scars, and skinfolds, or a combination thereof.

In some embodiments, the method further includes a vascular access site-defining step of defining the historical sites of vascular access in the target data file by a number of needle-stick points in relation to the feature points. The needle-stick points correspond to needle-stick locations identified in the one-or-more images, video frames, or the combination thereof during a vascular-access procedure or manually entered into the alternative-reality device by the user after the vascular-access procedure.

In some embodiments, the graphical element-displaying step includes displaying visually differentiated graphical elements for at least successful sites of vascular access and unsuccessful sites of vascular access among the historical sites of vascular access.

In some embodiments, the successful sites of vascular access are represented on the display screen by green dots anchored to the anatomical portion of the patient and the unsuccessful sites of vascular access are represented on the display screen by red dots anchored to the anatomical portion of the patient.

In some embodiments, the method further includes a vascular access site-suggesting step. The vascular access site-suggesting step includes suggesting to the user a number of potential sites for vascular access on the display screen with the one-or-more graphical elements in view of the historical sites of vascular access. The vascular access site-suggesting step is performed upon executing vascular access site-suggesting logic stored in the memory of the alternative-reality device by the one-or-more processors.

In some embodiments, the method further includes a data-transferring step. The data-transferring step includes wirelessly transferring the target data file to a network-connected computer system with a wireless communication module of the alterative-reality device for updating an electronic medical record.

In some embodiments, the alterative-reality device is a headset. The display screen of the headset is a see-through display screen through which the user can see the environment including the patient.

In some embodiments, the alternative-reality device is a smartphone. The display screen of the smartphone is a built-in display screen upon which the user can see the environment including the patient.

Also disclosed herein is a method for establishing and visualizing historical sites of vascular access. The method includes a device-obtaining step, a capturing step, and a display screen-viewing step. The device-obtaining step includes obtaining an alternative-reality device. The alternative-reality device includes anatomical target-defining instructions and vascular access site-tracking instructions in memory of the alternative-reality device for execution by the one-or-more processors of the alternative-reality device. The capturing step includes capturing an anatomical portion of a patient in one or more images, video frames, or a combination thereof with a patient-facing camera of the alternative-reality device. The capturing step allows the alternative-reality device to generate an anatomical target in a corresponding target data file in the memory in accordance with the anatomical target-defining instructions. The capturing step also allows the alternative-reality device to track sites of vascular access with respect to the anatomical target in accordance with the vascular access site-tracking instructions. The display screen-viewing step includes viewing an environment including the anatomical portion of the patient by way of a display screen of the alternative-reality device. The display screen-viewing step also includes viewing one or more graphical elements on the display screen anchored to the anatomical portion of the patient to indicate at least historical sites of vascular access.

In some embodiments, the one-or-more graphical elements are visually differentiated among at least graphical elements for successful sites of vascular access and unsuccessful sites of vascular access among the historical sites of vascular access.

In some embodiments, the successful sites of vascular access are represented on the display screen by green dots anchored to the anatomical portion of the patient and the unsuccessful sites of vascular access are represented on the display screen by red dots anchored to the anatomical portion of the patient.

In some embodiments, the method further includes a vascular access site-evaluating step and a vascular access site-selecting step. The vascular access site-evaluating step includes evaluating the historical sites of vascular access. The vascular access site-selecting step includes selecting a potential site of vascular access in view of the historical sites of vascular access.

In some embodiments, the method further includes a vascular access site-selecting step. The vascular access site-selecting step includes selecting a potential site of vascular access from the potential sites for vascular access indicated by the one-or-more graphical elements on the display screen. The potential sites for vascular access are suggested by the alternative-reality device upon execution of vascular access site-suggesting logic stored in the memory of the alternative-reality device by the one-or-more processors.

These and other features of the concepts provided herein will become more apparent to those of skill in the art in view of the accompanying drawings and following description, which describe particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "alternative reality," alternative reality includes virtual reality, augmented reality, and mixed reality unless context suggests otherwise. "Virtual reality" includes virtual content in a virtual setting, which setting can be a fantasy or a real-world simulation. "Augmented reality" and "mixed reality" include virtual content in a real-world setting. Augmented reality includes the virtual content in the real-world setting, but the virtual content is not necessarily anchored in the real-world setting. For example, the virtual content can be information overlying the real-world setting. The information can change as the real-world setting changes due to time or environmental conditions in the real-world setting, or the information can change as a result of an experiencer of the augmented reality moving through the real-world setting—but the information remains overlying the real-world setting. Mixed reality includes the virtual content anchored in every dimension of the real-world setting. For example, the virtual content can be a virtual object anchored in the real-world setting. The virtual object can change as the real-world setting changes due to time or environmental conditions in the real-world setting, or the virtual object can change to accommodate the perspective of an experiencer of the mixed reality as the experiencer moves through the real-world setting. The virtual object can also change in accordance with any interactions with the experiencer or another real-world or virtual agent. Unless the virtual object is moved to another location in the real-world setting by the experiencer of the mixed reality, or some other real-world or virtual agent, the virtual object remains anchored in the real-world setting. Mixed reality does not exclude the foregoing information overlying the real-world setting described in reference to augmented reality.

Unless defined otherwise, all technical and scientific terms used herein have the same meaning as commonly understood by those of ordinary skill in the art.

As set forth above, vascular access is not always so easily obtained. For example, vascular access can be particularly difficult to obtain if a patient is older, obese, or hypotensive. It can also be particularly difficult to obtain vascular access if the patient is an intravenous drug abuser or has one or more injuries limiting potential sites for vascular access. It would be helpful to instantly visualize historical sites of vascular access and the successes and failures thereof in obtaining vascular access.

Disclosed herein are alternative-reality devices and methods for establishing and visualizing historical sites of vascular access, which are useful for evaluating potential sites for vascular access and improving the successes of obtaining vascular access.

Alternative-Reality Device

Figure 4:
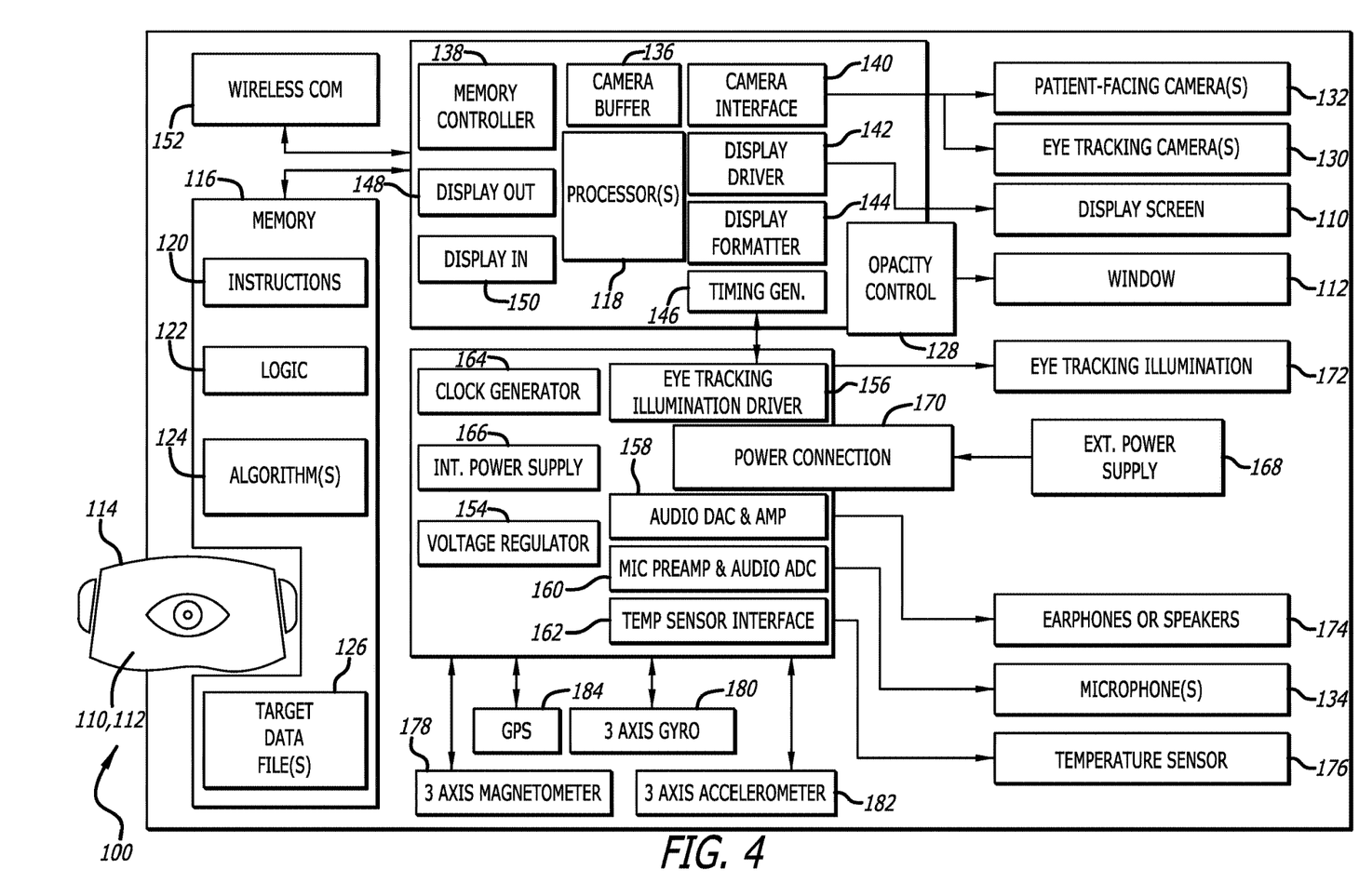
FIG. 4 illustrates a block diagram of an alternative-reality headset in accordance with some embodiments.

An alternative-reality device for establishing and visualizing historical sites of vascular access can include, in some embodiments, a smartphone, an alternative-reality headset 100 as shown in FIG. 4, or a single-purpose device configured for establishing and visualizing historical sites of vascular access. The alternative-reality headset 100 is set forth in detail below; however, the alternative-reality device is first set forth in terms inclusive of the foregoing embodiments of the alternative-reality device.

The alternative-reality device includes a mechanical support, one or more patient-facing cameras (e.g., the one-or-more patient-facing cameras 132) operably coupled to the mechanical support, and a display screen (e.g., the display screen 110) operably coupled to the mechanical support.

The mechanical support supports electronic components including one or more processors (e.g., the one-or-more processors 118) and memory (e.g., the memory 116) communicatively coupled by electronic circuitry of the alternative-reality device. With respect to a smartphone, the mechanical support can be a printed circuit board disposed in a housing of the smartphone. With respect to the alternative-reality headset 100, the mechanical support can be a printed circuit board disposed in the frame 114 of the alternative-reality headset 100.

Figure 1A:
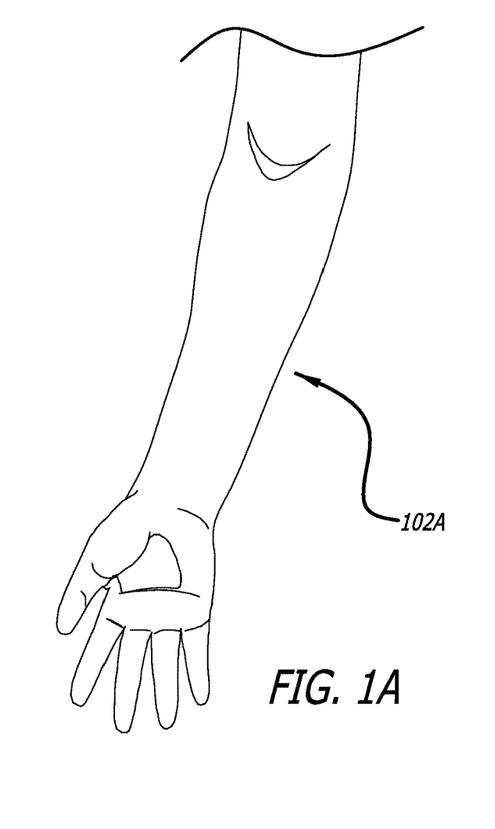
FIG. 1A illustrates an anatomical portion of a patient in accordance with some embodiments.
Figure 2A:
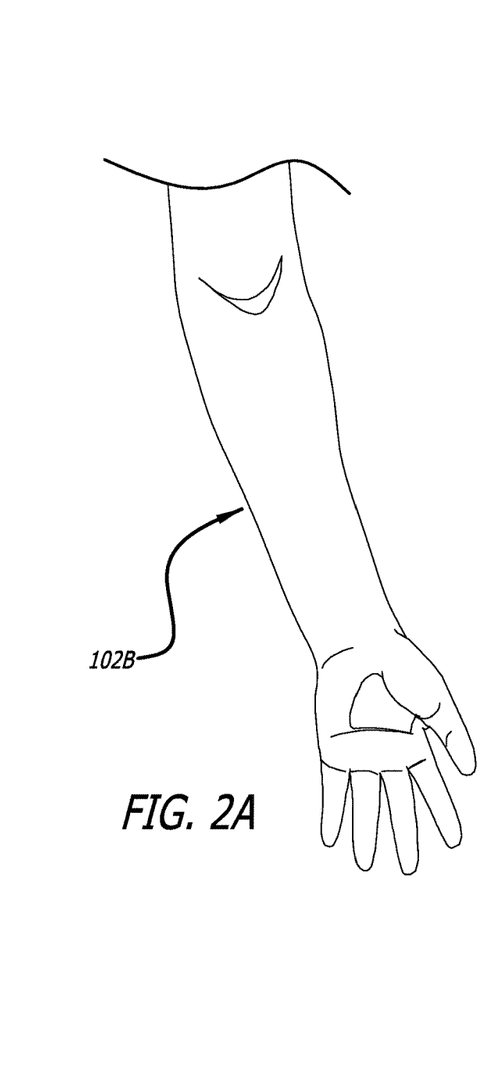
FIG. 2A illustrates an anatomical portion of another patient in accordance with some embodiments.
Figure 3A:
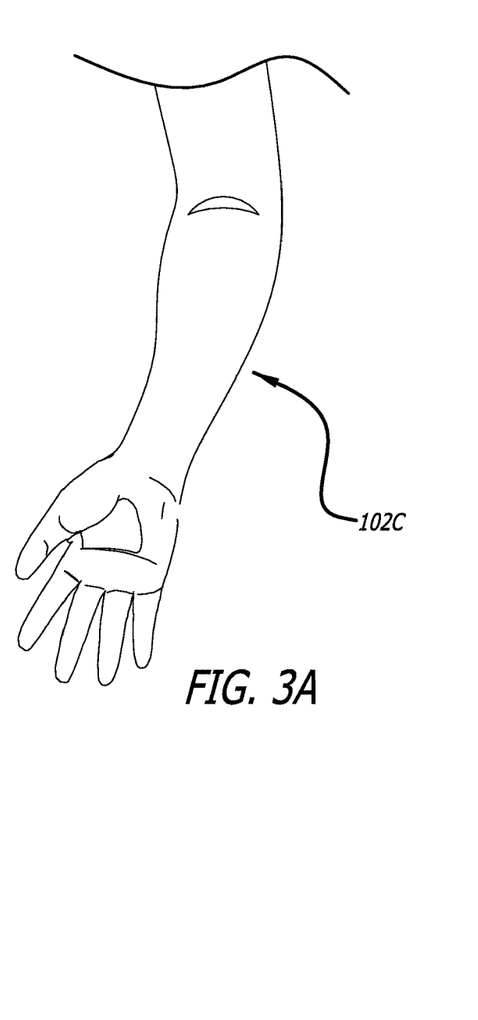
FIG. 3A illustrates an anatomical portion of yet another patient in accordance with some embodiments.

FIGS. 1A, 2A, and 3A respectively illustrate an anatomical portion 102A, 102B, and 102C (hereinafter, "the anatomical portion 102") of a first, second, and third patient in accordance with some embodiments.

The one-or-more patient-facing cameras are configured to capture one or more images, video frames, or a combination thereof including that of the anatomical portion 102 (e.g., an arm, a leg, etc.) of the patient. As set forth below, the one-or-more images, video frames, or the combination thereof are at least for generating the anatomical target from the anatomical portion 102 of the patient in accordance with the anatomical target-defining instructions. The one-or-more images, video frames, or the combination thereof are also at least for tracking the historical sites of vascular access 106 in relation to the anatomical target in accordance with the vascular access site-tracking instructions.

The memory includes stored therein instructions (e.g., the instructions 120), logic (e.g., the logic 122), and data (e.g., the target data files 126) for establishing and visualizing historical sites of vascular access. The instructions can include anatomical target-defining instructions and vascular access site-tracking instructions for execution by the one-or-more processors. The logic can include vascular access site-suggesting logic for execution by the one-or-more processors. Various computer-vision algorithms (e.g., part of the one-or-more algorithms 124) needed for image recognition, video recognition, video tracking, or the like can also be stored in the memory for execution by the one-or-more processors.

Figure 1B:
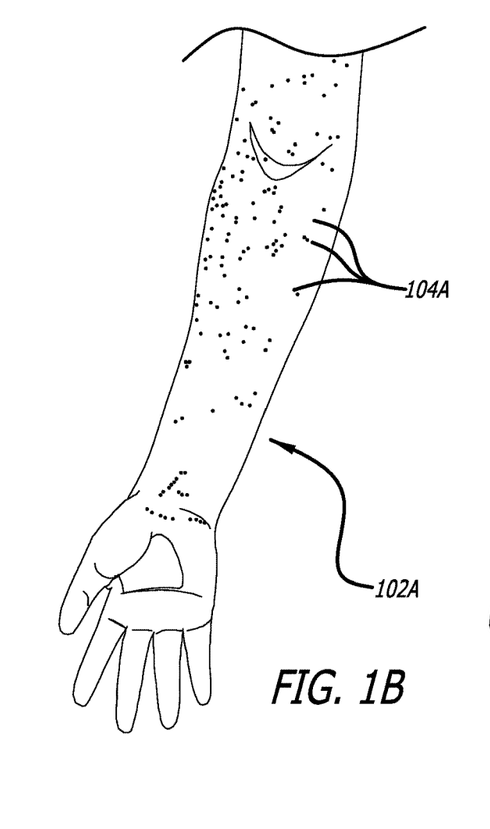
FIG. 1B illustrates a number of feature points corresponding to anatomical features identified in one-or-more images or video frames in accordance with some embodiments.
Figure 2B:
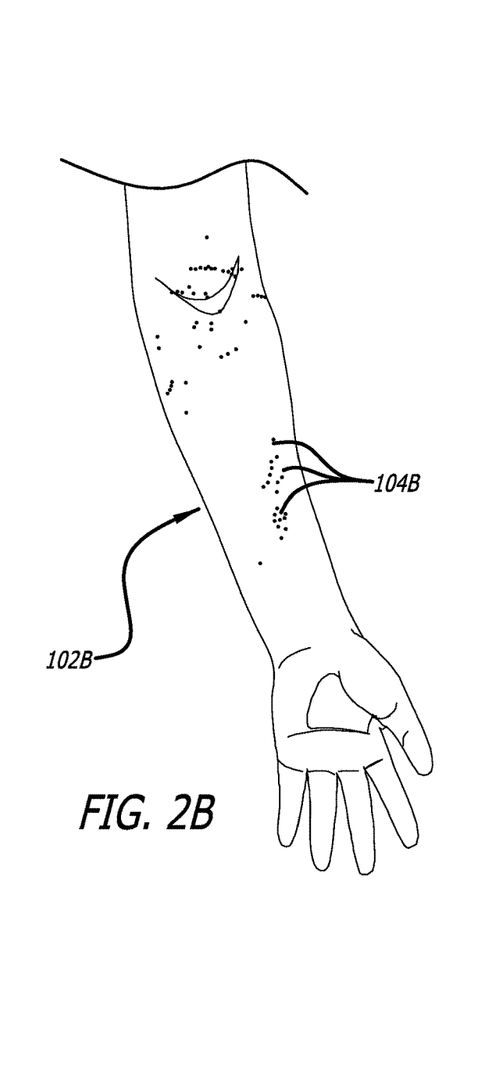
FIG. 2B illustrates another number of feature points corresponding to anatomical features identified in one-or-more images or video frames in accordance with some embodiments.
Figure 3B:
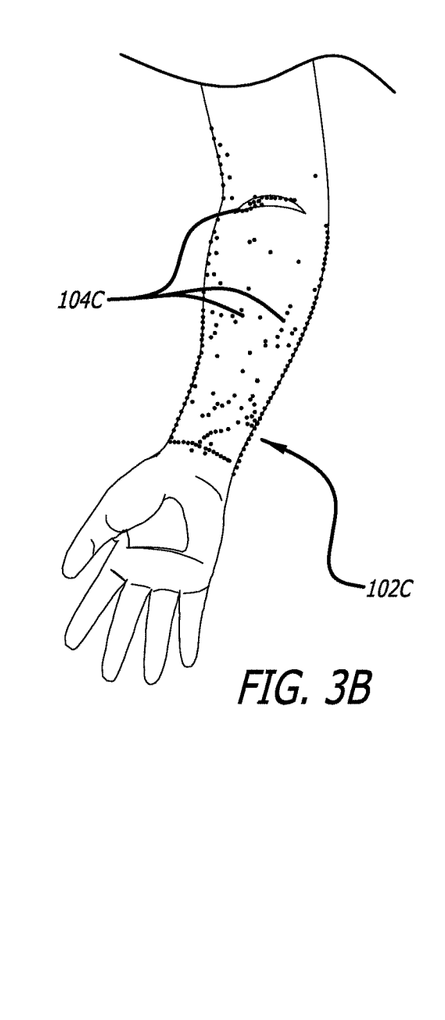
FIG. 3B illustrates yet another number of feature points corresponding to anatomical features identified in one-or-more images or video frames in accordance with some embodiments.

FIGS. 1B, 2B, and 3B respectively illustrate a number of feature points 104A, 104B, and 104C (hereinafter, "the feature points 104") corresponding to anatomical features identified in the one-or-more images, video frames, or the combination thereof in accordance with some embodiments. While the feature points 104 are conveniently indicated by way of dots in FIGS. 1B, 2B, and 3B, it should be understood the feature points 104 exist independently of any such graphical display of the feature points.

The anatomical target-defining instructions are configured to generate an anatomical target from the anatomical portion 102 of the patient in the one-or-more images, video frames, or the combination thereof in a corresponding target data file (e.g., the target data files 126) in the memory. The anatomical target is defined in the target data file by the feature points 104, which are mutually referential points corresponding to anatomical features identified (e.g., by the various computer-vision algorithms including those for image recognition, video recognition, and video tracking) in the one-or-more images, video frames, or the combination thereof for the anatomical portion 102 of the patient. The anatomical features can include topographical features selected from veins, moles, scars, and skinfolds, of which the veins, moles, and scars can be protruding features that protrude from a surface of the anatomical portion 102 of the patient. Skinfolds and even some scars can be recessed features that are recessed into the surface of the anatomical portion 102 of the patient. The anatomical features can also include skin-contrasting features selected from veins, moles, scars, and skinfolds, or a combination thereof.

Figure 1C:
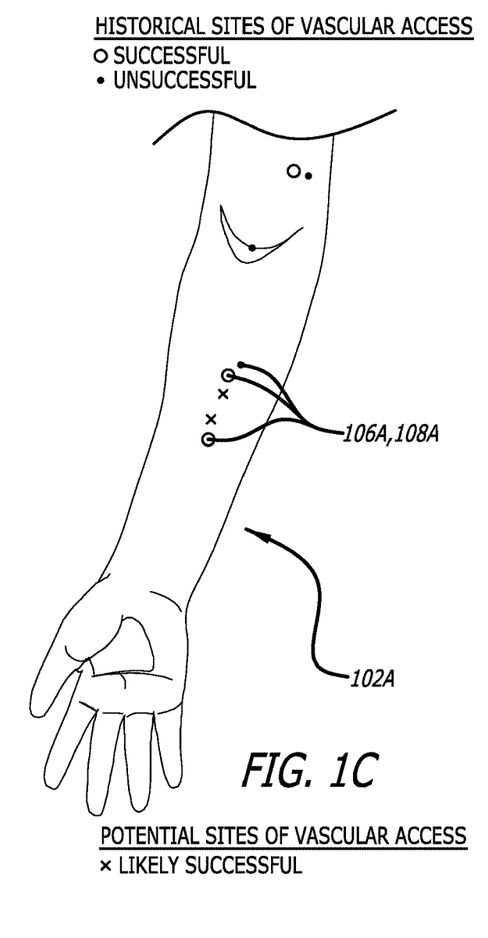
FIG. 1C illustrates a number of historical sites of vascular access in accordance with some embodiments.
Figure 2C:
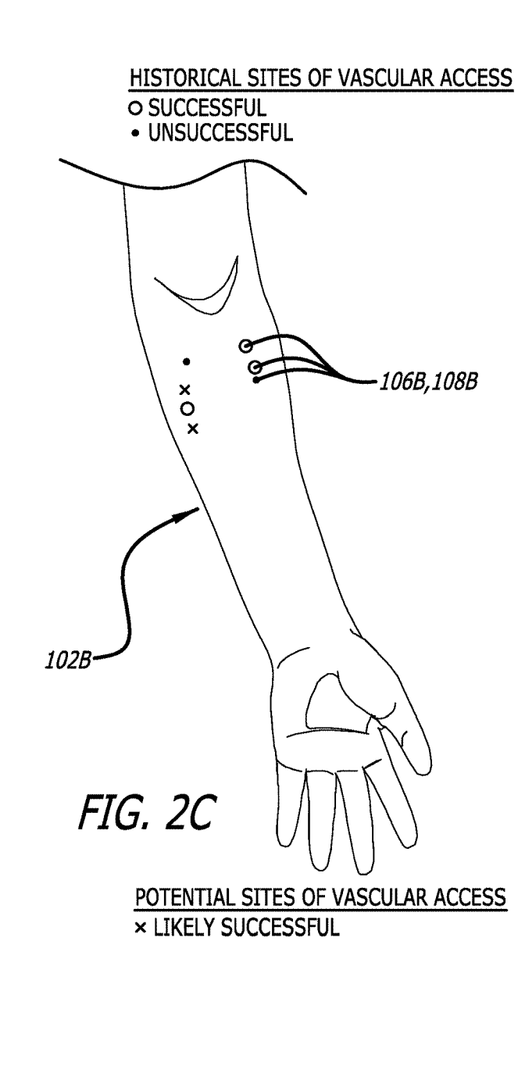
FIG. 2C illustrates another number of historical sites of vascular access in accordance with some embodiments.
Figure 3C:
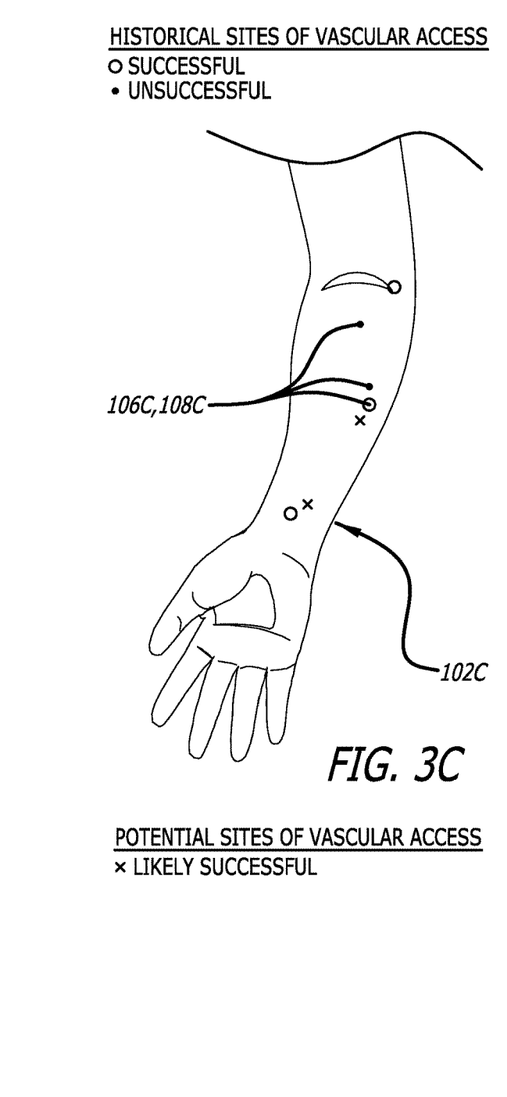
FIG. 3C illustrates another number of historical sites of vascular access in accordance with some embodiments.

FIGS. 1C, 2C, and 3C respectively illustrate a number of historical sites of vascular access 106A, 106B, and 106C (hereinafter, "the historical sites of vascular access 106") in accordance with some embodiments. While the historical sites of vascular access 106 are conveniently indicated by way of the one-or-more graphical elements 108 set forth below, it should be understood the historical sites of vascular access 106 exist independently of the one-or-more graphical elements 108. Indeed, the one-or-more graphical elements 108 represent the historical sites of vascular access 106 on the display screen 110 of alternative-reality device.

The vascular access site-tracking instructions are configured to track the historical sites of vascular access 106 from the one-or-more images, video frames, or the combination thereof in relation to the anatomical target. The historical sites of vascular access 106 are defined in the target data file or another file associated therewith by a number of needle-stick points in relation to the feature points 104. (See FIGS. 1C, 2C, and 3C for the one-or-more graphical elements 108 corresponding to such needle-stick points.) The needle-stick points correspond to needle-stick locations identified (e.g., by the various computer-vision algorithms including those for image recognition, video recognition, and video tracking) in the one-or-more images, video frames, or the combination thereof during a vascular-access procedure. Alternatively, the needle-stick points are manually entered into the alternative-reality device by a user (e.g., a clinician) thereof after the vascular-access procedure.

With the display screen, the user of the alternative-reality device can instantly see the environment including the anatomical portion 102 of the patient to which the anatomical target corresponds. The display screen is configured to display one or more graphical elements 108A, 108B, and 108C (hereinafter, "the one-or-more graphical elements 108") anchored (e.g., by way of a mixed-reality experience) to the anatomical portion 102 of the patient to indicate at least the historical sites of vascular access 106. The one-or-more graphical elements 108 for the historical sites of vascular access 106 are visually differentiated among at least graphical elements for successful sites of vascular access and unsuccessful sites of vascular access among the historical sites of vascular access 106. For example, the successful sites of vascular access can be represented on the display screen by green dots anchored to the anatomical portion 102 of the patient, while the unsuccessful sites of vascular access can be represented on the display screen by red dots anchored to the anatomical portion 102 of the patient.

FIGS. 1C, 2C, and 3C also respectively illustrate a number of potential sites for vascular access in accordance with some embodiments.

The vascular access site-suggesting logic is configured to suggest to the user a number of potential sites for vascular access on the display screen with the one-or-more graphical elements 108 in view of the historical sites of vascular access 106. The one-or-more graphical elements 108 for the potential sites for vascular access are visually differentiated from those of the historical sites of vascular access 106. For example, the potential sites for vascular access can be represented on the display screen by yellow crosses or arrows anchored to the anatomical portion 102 of the patient. With respect to a smartphone, the display screen can be a built-in display screen coupled to the housing upon which the user can see the environment including the patient. With respect to the alternative-reality headset 100, the display screen can be a see-through display screen (i.e., the display screen 110) coupled to the frame 114 through which the user can see the environment including the patient.

The alternative-reality device can further include a wireless communication module (e.g., the wireless communications interface 152) for wirelessly transferring the target data file and any supporting or related data to a network-connected computer system and updating an electronic medical record of the patient.

FIG. 4 illustrates a block diagram of the alternative-reality headset 100 in accordance with some embodiments.

As shown, the alternative-reality headset 100, which can have a goggle-type or face shield-type form factor, includes a suitably configured display screen 110 and a window 112 thereover coupled to a frame 114 having electronic circuitry including memory 116 and one or more processors 118. The memory includes stored therein instructions 120 (e.g., the anatomical target-defining instructions, the vascular access site-tracking instructions, etc.), logic 122 (e.g., the vascular access site-suggesting logic, etc.), one or more algorithms 124, and data such as the target data files 126 for establishing and visualizing historical sites of vascular access. The display screen 110 is configured such that a wearer of the alternative-reality headset 100 can see the environment (e.g., room) including the patient through the display screen 110 in accordance with an opacity of the window 112, which opacity is adjustable with an opacity control 128. The display screen 110 is configured to display the one-or-more graphical elements 108 anchored to the anatomical portion 102 of the patient in three dimensions in the environment, which is characteristic of mixed reality. (See, for example, FIGS. 1C, 2C, and 3C.)

The alternative-reality headset 100 can further include a perceptual user interface ("PUI") configured to enable the wearer of the alternative-reality headset 100 to interact with the alternative-reality headset 100 without a physical input device such as keyboard or mouse. Instead of a physical input device, the PUI can have input devices including, but not limited to, one or more wearer-facing eye-tracking cameras 130, one or more patient-facing cameras 132, one or more microphones 134, or a combination thereof. At least one advantage of the PUI and the input devices thereof is that the clinician does not have to reach outside a sterile field to execute a command of the alternative-reality headset 100.

With respect to the one-or-more eye-tracking cameras 130, the one-or-more eye-tracking cameras 130 can be coupled to the frame 114 and configured to capture eye movements of the wearer in a camera buffer 136 or the memory 116. The one-or-more processors 118 of the alternative-reality headset 100 can be configured to process the eye movements with an eye-movement algorithm of the one-or-more algorithms 124 to identify a focus of the wearer. For example, the focus of the wearer can be used by the PUI to select a graphical element for a historical site of vascular access, which, in turn, can invoke the display of overlying historical information (e.g., time, date, place, reason for failure, etc.) for the historical site of vascular access.

With respect to the one-or-more patient-facing cameras 132, the one-or-more patient-facing cameras 132 can be coupled to the frame 114 and configured to capture the one-or-more images, video frames, or the combination thereof for generating the anatomical target from the anatomical portion 102 of the patient and tracking the historical sites of vascular access 106 in relation to the anatomical target. With respect to the PUI, the one-or-more patient-facing cameras 132 can be configured to capture gestures of the wearer in the camera buffer 136 or the memory 116. The one-or-more processors 118 of the alternative-reality headset 100 can be configured to process the gestures with a gesture-command algorithm of the one-or-more algorithms 124 to identify gesture-based commands issued by the wearer for execution thereof by the alternative-reality headset 100.

With respect to the one-or-more microphones 134, the one-or-more microphones 134 can be coupled to the frame 114 and configured to capture audio of the wearer in the memory 116. The one-or-more processors 118 of the alternative-reality headset 100 can be configured to process the audio with an audio-command algorithm of the one-or-more algorithms 124 to identify audio-based PUI commands issued by the wearer for execution thereof by the alternative-reality headset 100.

The electronic circuitry includes the one-or-more processors 118, a memory controller 138 in communication with the memory 116 (e.g., dynamic random-access memory ["DRAM"]), a camera interface 140, the camera buffer 136, a display driver 142, a display formatter 144, a timing generator 146, a display-out interface 148, and a display-in interface 150. Such components can be in communication with each other through the one-or-more processors 118, dedicated lines of one or more buses, or a combination thereof.

The camera interface 140 is configured to provide an interface to the one-or-more eye-tracking cameras 130 and the one-or-more patient-facing cameras 132, as well as store respective images, video frames, or a combination thereof received from the eye-tracking and patient-facing cameras 130 and 132 in the camera buffer 136 or the memory 116. Each camera of the one-or-more eye-tracking cameras 130 can be an infrared ("IR") camera or a position-sensitive detector ("PSD") configured to track eye-glint positions by way of IR reflections or eye glint-position data, respectively.

The display driver 142 is configured to drive the display screen 110. The display formatter 144 is configured to provide display-formatting information for at least the one-or-more graphical elements 108 to the one-or-more processors 118 for formatting the one-or-more graphical elements 108 for display on the display screen 110 anchored to the anatomical portion 102 of the patient. The timing generator 146 is configured to provide timing data for the alternative-reality headset 100. The display-out interface 148 includes a buffer for providing the one-or-more images, video frames, or the combination thereof from the one-or-more patient-facing cameras 132 to another computer system. The display-in interface 150 includes a buffer for receiving any other images or video frames from the other computer system to be displayed on the display screen 110. Notwithstanding the foregoing, the foregoing images and video frames, or any other data for that matter, can be transferred between the alternative-reality headset 100 and the other computer by way of a wireless communications interface 152. The opacity control 128 is configured to change a degree of opacity of the window 112.

Additional electronic circuitry includes a voltage regulator 154, an eye-tracking illumination driver 156, an audio digital-to-analog converter ("DAC") and amplifier 158, a microphone preamplifier and audio analog-to-digital converter ("ADC") 160, a temperature-sensor interface 162, and a clock generator 164. The voltage regulator 154 is configured to receive power from an internal power supply 166 (e.g., a battery) or an external power supply 168 through a power connection 170. The voltage regulator 154 is configured to provide the received power to the electronic circuitry of the alternative-reality headset 100. The eye-tracking illumination driver 156 is configured to control an eye-tracking illumination unit 172 by way of a drive current or voltage to operate about a predetermined wavelength or within a predetermined wavelength range. The audio DAC and amplifier 158 is configured to provide audio data to earphones or speakers 174. The microphone preamplifier and audio ADC 160 is configured to provide an interface for the one-or-more microphones 134. The temperature-sensor interface 162 is configured as an interface for a temperature sensor 176. In addition, the alternative-reality headset 100 can include orientation sensors including a three-axis magnetometer 178, a three-axis gyroscope 180, and a three-axis accelerometer 182 configured to provide orientation-sensor data for determining an orientation of the alternative-reality headset 100 at any given time. Furthermore, the alternative-reality headset 100 can include a global-positioning system ("GPS") receiver 184 configured to receive GPS data (e.g., time and position information for one or more GPS satellites) for determining a location of the alternative-reality headset 100 at any given time.

Methods

Methods for establishing and visualizing historical sites of vascular access include methods implemented by the alternative-reality device itself, as well as methods of using the alternative-reality device.

A method implemented by the alternative-reality device (e.g., the alternative-reality headset 100) can include an anatomical target-generating step, an anatomical target-storing step, a vascular access site-tracking step, and a displaying step.

The anatomical target-generating step includes generating an anatomical target from an anatomical portion (e.g., the anatomical portion 102) of a patient in one or more images, video frames, or a combination thereof obtained from the one-or-more patient-facing cameras (e.g., the one-or-more patient-facing cameras 132) of the alternative-reality device. The anatomical target-generating step includes an anatomical target-defining step of defining (e.g., by the various computer-vision algorithms including those for image recognition, video recognition, and video tracking) the anatomical target in a target data file by a number of feature points (e.g., the feature points 104A, 104B, and 104C of FIGS. 1B, 2B, and 3B) corresponding to anatomical features of the anatomical portion 102 of the patient identified in the one-or-more images, video frames, or the combination thereof. Again, the anatomical features include topographical features selected from veins, moles, scars, and skinfolds, skin-contrasting features selected from veins, moles, scars, and skinfolds, or a combination thereof. The anatomical target-generating step is performed upon executing the anatomical target-defining instructions stored in the memory (e.g., the memory 116) of the alternative-reality device by the one-or-more processors thereof (e.g., the one-or-more processors 118).

The anatomical target-storing step includes storing the anatomical target in a corresponding target data file in the memory.

The vascular access site-tracking step includes tracking sites of vascular access from the one-or-more images, video frames, or the combination thereof in relation to the anatomical target in the target data file. The vascular access site-tracking step includes a vascular access site-defining step of defining (e.g., by the various computer-vision algorithms including those for image recognition, video recognition, and video tracking) the historical sites of vascular access 106 in the target data file or another file associated therewith by a number of needle-stick points in relation to the feature points 104. The needle-stick points correspond to needle-stick locations identified in the one-or-more images, video frames, or the combination thereof during a vascular-access procedure or manually entered into the alternative-reality device by a user (e.g., a clinician) of the alternative-reality device after the vascular-access procedure. The vascular access site-tracking step is performed upon executing the vascular access site-tracking instructions stored in the memory by the one-or-more processors.

The graphical element-displaying step includes displaying on the display screen (e.g., the display screen 110) of the alternative-reality device one or more graphical elements (e.g., the one-or-more graphical elements 108) anchored (e.g., by way of a mixed-reality experience) to the anatomical portion 102 of the patient in an environment thereof to indicate to the user at least the historical sites of vascular access 106. The graphical element-displaying step includes displaying visually differentiated graphical elements for at least the successful sites of vascular access and the unsuccessful sites of vascular access among the historical sites of vascular access 106. As set forth above, the successful sites of vascular access can be represented on the display screen by green dots anchored to the anatomical portion 102 of the patient and the unsuccessful sites of vascular access can be represented on the display screen by red dots anchored to the anatomical portion 102 of the patient.

The method can further includes a vascular access site-suggesting step. The vascular access site-suggesting step includes suggesting to the user a number of potential sites for vascular access on the display screen with the one-or-more graphical elements 108 in view of the historical sites of vascular access 106. As set forth above, the potential sites for vascular access can be represented on the display screen by yellow crosses or arrows anchored to the anatomical portion 102 of the patient. The vascular access site-suggesting step is performed upon executing vascular access site-suggesting logic stored in the memory of the alternative-reality device by the one-or-more processors.

The method can further include a data-transferring step. The data-transferring step includes wirelessly transferring the target data file to a network-connected computer system with the wireless communication module (e.g., the wireless communications interface 152) of the alternative-reality device for updating an electronic medical record of the patient.

A method of using the alternative-reality device (e.g., the alternative-reality headset 100) can include a device-obtaining step, a capturing step, and a display screen-viewing step.

The device-obtaining step includes obtaining the alternative-reality device. As set forth above, the alternative-reality device includes the anatomical target-defining instructions and the vascular access site-tracking instructions in the memory of the alternative-reality device for execution by the one-or-more processors of the alternative-reality device.

The capturing step includes capturing an anatomical portion (e.g., the anatomical portion 102) of a patient in one or more images, video frames, or a combination thereof with the one-or-more patient-facing cameras (e.g., the one-or-more patient-facing cameras 132) of the alternative-reality device. The capturing step allows the alternative-reality device to generate an anatomical target in a corresponding target data file in the memory in accordance with the anatomical target-defining instructions. The capturing step also allows the alternative-reality device to track sites of vascular access with respect to the anatomical target in accordance with the vascular access site-tracking instructions.

The display screen-viewing step includes viewing an environment including the anatomical portion 102 of the patient by way of the display screen (e.g., the display screen 110) of the alternative-reality device. The display screen-viewing step also includes viewing one or more graphical elements (e.g., the one-or-more graphical elements 108) on the display screen anchored (e.g., by way of a mixed-reality experience) to the anatomical portion 102 of the patient to indicate at least the historical sites of vascular access 106. As set forth above, the one-or-more graphical elements 108 are visually differentiated among at least graphical elements for the successful sites of vascular access and the unsuccessful sites of vascular access among the historical sites of vascular access 106. As set forth above, the successful sites of vascular access can be represented on the display screen by green dots anchored to the anatomical portion 102 of the patient and the unsuccessful sites of vascular access can be represented on the display screen by red dots anchored to the anatomical portion 102 of the patient.

The method can further include a vascular access site-evaluating step. The vascular access site-evaluating step includes evaluating the historical sites of vascular access 106 including, for example, any overlying historical information (e.g., time, date, place, reason for failure, etc.) for the historical sites of vascular access 106 provided by the PUI of the alternative-reality headset 100. A vascular access site-selecting step can follow the vascular access site-evaluating step. Such a vascular access site-selecting step includes selecting a potential site of vascular access in view of the historical sites of vascular access 106 evaluated in the vascular access site-evaluating step. However, the vascular access site-selecting step need not follow the vascular access site-evaluating step. Indeed, the vascular access site-selecting step can include selecting a potential site of vascular access from potential sites for vascular access indicated by the one-or-more graphical elements 108 (e.g., the yellow crosses of arrows set forth above) on the display screen. The potential sites for vascular access are suggested by the alternative-reality device upon execution of the vascular access site-suggesting logic stored in the memory of the alternative-reality device by the one-or-more processors.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An alternative-reality device for establishing and visualizing historical sites of vascular access, the alternative-reality device comprising:
   a mechanical support supporting electronic components including memory and one or more processors communicatively coupled by electronic circuitry of the alternative-reality device, the memory including anatomical target-defining instructions and vascular access site-tracking instructions for execution by the one or more processors;
   a patient-facing camera operably coupled to the mechanical support, the patient-facing camera configured to capture one or more images, video frames, or a combination thereof for generating an anatomical target in a corresponding target data file in the memory and tracking the historical sites of vascular access in relation to the anatomical target in accordance with the anatomical target-defining instructions and the vascular access site-tracking instructions, respectively, wherein the historical sites of vascular access are defined in the corresponding target data file by a number of needle-stick points in relation to a number of feature points corresponding to anatomical features identified in the one or more images, video frames, or the combination thereof, the number of needle-stick points corresponding to needle-stick locations identified in the one or more images, video frames, or the combination thereof during a vascular-access procedure or manually entered into the alternative-reality device by a user after the vascular-access procedure; and
   a display screen operably coupled to the mechanical support with which a user of the alternative-reality device can instantly see an environment including an anatomical portion of a patient to which the anatomical target corresponds, the display screen configured to display one or more graphical elements anchored to the anatomical portion of the patient to indicate at least the historical sites of vascular access.

2. The alternative-reality device of claim 1, wherein the anatomical features include topographical features selected from veins, moles, scars, and skinfolds, or skin-contrasting features selected from veins, moles, scars, and skinfolds, or a combination thereof.

3. The alternative-reality device of claim 1, wherein the one or more graphical elements are visually differentiated among at least graphical elements for successful sites of vascular access and unsuccessful sites of vascular access among the historical sites of vascular access.

4. The alternative-reality device of claim 3, wherein the successful sites of vascular access are represented on the display screen by green dots anchored to the anatomical portion of the patient and the unsuccessful sites of vascular access are represented on the display screen by red dots anchored to the anatomical portion of the patient.

5. The alternative-reality device of claim 3, the memory further including vascular access site-suggesting logic for execution by the one or more processors, the vascular access site-suggesting logic configured to suggest to the user a number of potential sites for vascular access on the display screen with the one or more graphical elements in view of the historical sites of vascular access.

6. The alternative-reality device of claim 1, wherein the alternative-reality device is a headset, the mechanical support being a printed circuit board disposed in a frame of the headset, and the display screen being a see-through display screen coupled to the frame through which the user can see the environment including the patient.

7. The alternative-reality device of claim 1, wherein the alternative-reality device is a smartphone, the mechanical support being a printed circuit board disposed in a housing of the smartphone, and the display screen being a built-in display screen coupled to the housing upon which the user can see the environment including the patient.

8. The alternative-reality device of claim 1, wherein the alternative-reality device includes a wireless communication module for wirelessly transferring the corresponding target data file to a network-connected computer system and updating an electronic medical record.

9. A method of an alternative-reality device, comprising:
   generating an anatomical target from an anatomical portion of a patient in one or more images, video frames, or a combination thereof obtained from a patient-facing camera of the alternative-reality device upon executing anatomical target-defining instructions stored in memory of the alternative-reality device by one or more processors thereof;
   storing the anatomical target in a corresponding target data file in the memory, wherein generating the anatomical target includes defining the anatomical target in the corresponding target data file by a number of feature points corresponding to anatomical features of the anatomical portion of the patient identified in the one or more images, video frames, or the combination thereof;
   tracking sites of vascular access from the one or more images, video frames, or the combination thereof upon executing vascular access site-tracking instructions stored in the memory by the one or more processors, the tracking of the sites of vascular access in relation to the anatomical target in the corresponding target data file;
   displaying on a display screen of the alternative-reality device one or more graphical elements anchored to the anatomical portion of the patient in an environment thereof to indicate to a user of the alternative-reality device at least historical sites of vascular access; and defining the at least historical sites of vascular access in the corresponding target data file by a number of needle-stick points in relation to the number of feature points, the number of needle-stick points corresponding to needle-stick locations identified in the one or more images, video frames, or the combination thereof during a vascular-access procedure or manually entered into the alternative-reality device by the user after the vascular-access procedure.

10. The method of claim 9, wherein the anatomical features include topographical features selected from veins, moles, scars, and skinfolds, or skin-contrasting features selected from veins, moles, scars, and skinfolds, or a combination thereof.

11. The method of claim 9, wherein displaying the one or more graphical elements includes displaying visually differentiated graphical elements for at least successful sites of vascular access and unsuccessful sites of vascular access among the at least historical sites of vascular access.

12. The method of claim 11, wherein the at least successful sites of vascular access are represented on the display screen by green dots anchored to the anatomical portion of the patient and the unsuccessful sites of vascular access are represented on the display screen by red dots anchored to the anatomical portion of the patient.

13. The method of claim 11, further comprising suggesting to the user a number of potential sites for vascular access on the display screen with the one or more graphical elements in view of the at least historical sites of vascular access, the suggesting of the number of potential sites for vascular access performed upon executing vascular access-site-suggesting logic stored in the memory of the alternative-reality device by the one or more processors.

14. The method of claim 9, further comprising wirelessly transferring the corresponding target data file to a network-connected computer system with a wireless communication module of the alternative-reality device for updating an electronic medical record.

15. The method of claim 9, wherein the alternative-reality device is a headset, the display screen being a see-through display screen through which the user can see the environment including the patient.

16. The method of claim 9, wherein the alternative-reality device is a smartphone, the display screen being a built-in display screen upon which the user can see the environment including the patient.

17. A method for establishing and visualizing historical sites of vascular access, comprising:
obtaining an alternative-reality device including anatomical target-defining instructions and vascular access site-tracking instructions in memory of the alternative-reality device for execution by one or more processors of the alternative-reality device;
capturing an anatomical portion of a patient in one or more images, video frames, or a combination thereof with a patient-facing camera of the alternative-reality device, thereby allowing the alternative-reality device to generate an anatomical target in a corresponding target data file in the memory, and track sites of vascular access with respect to the anatomical target in accordance with the anatomical target-defining instructions and the vascular access site-tracking instructions, respectively,
wherein the historical sites of vascular access are defined in the corresponding target data file by a number of needle-stick points in relation to a number of feature points corresponding to anatomical features identified in the one or more images, video frames, or the combination thereof, the number of needle-stick points corresponding to needle-stick locations identified in the one or more images, video frames, or the combination thereof during a vascular-access procedure or manually entered into the alternative-reality device by a user after the vascular-access procedure; and
viewing an environment including the anatomical portion of the patient by way of a display screen of the alternative-reality device, as well as one or more graphical elements on the display screen anchored to the anatomical portion of the patient to indicate at least historical sites of vascular access.

18. The method of claim 17, wherein the one or more graphical elements are visually differentiated among at least graphical elements for successful sites of vascular access and unsuccessful sites of vascular access among the historical sites of vascular access.

19. The method of claim 18, wherein the successful sites of vascular access are represented on the display screen by green dots anchored to the anatomical portion of the patient and the unsuccessful sites of vascular access are represented on the display screen by red dots anchored to the anatomical portion of the patient.

20. The method of claim 17, further comprising evaluating the historical sites of vascular access and selecting a potential site of vascular access in view of the historical sites of vascular access.

21. The method of claim 17, further comprising selecting a potential site of vascular access from a number of potential sites for vascular access indicated by the one or more graphical elements on the display screen, the number of potential sites for vascular access suggested by the alternative-reality device upon execution of vascular access site-suggesting logic stored in the memory of the alternative-reality device by the one or more processors.

* * * * *